United States Patent
Birnbaum et al.

(10) Patent No.: US 9,501,149 B2
(45) Date of Patent: *Nov. 22, 2016

(54) SYSTEM FOR HAPTICALLY REPRESENTING SENSOR INPUT

(71) Applicant: Immersion Corporation, San Jose, CA (US)

(72) Inventors: David Birnbaum, Oakland, CA (US); Christopher J. Ullrich, Ventura, CA (US); Danny Grant, Laval (CA); Ali Modarres, San Jose, CA (US); Juan Manuel Cruz-Hernandez, Montreal (CA)

(73) Assignee: Immersion Corporation, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/819,880

(22) Filed: Aug. 6, 2015

(65) Prior Publication Data

US 2015/0338921 A1    Nov. 26, 2015

Related U.S. Application Data

(63) Continuation of application No. 13/597,300, filed on Aug. 29, 2012, now Pat. No. 9,116,546.

(51) Int. Cl.
| | |
|---|---|
| *G08B 6/00* | (2006.01) |
| *G09B 21/00* | (2006.01) |
| *H04B 3/36* | (2006.01) |
| *G06F 3/01* | (2006.01) |
| *A61B 5/00* | (2006.01) |

(52) U.S. Cl.
CPC .............. *G06F 3/016* (2013.01); *A61B 5/0002* (2013.01); *G08B 6/00* (2013.01); *G09B 21/003* (2013.01)

(58) Field of Classification Search
CPC .... G06F 3/016; G06F 19/3418; G06F 3/017; G06F 3/0202; G08B 6/00; G08B 25/10; G08B 21/22; G09B 21/003; A61B 5/0002
USPC ......... 340/4.12, 539.12, 407.1, 407.2, 573.1, 340/573.3, 575; 345/156, 158, 173
See application file for complete search history.

(56) References Cited

U.S. PATENT DOCUMENTS

| | | | | |
|---|---|---|---|---|
| 7,764,166 | B2 * | 7/2010 | King | G08B 6/00 340/4.12 |
| 7,898,396 | B2 * | 3/2011 | Ullrich | A61B 5/0002 340/407.1 |
| 8,004,391 | B2 * | 8/2011 | Cruz Hernandez | A61B 5/02438 340/407.1 |
| 8,217,769 | B2 * | 7/2012 | Ullrich | A61B 5/0002 340/407.1 |
| 8,279,193 | B1 * | 10/2012 | Birnbaum | G06F 3/016 340/407.2 |
| 8,301,108 | B2 * | 10/2012 | Naboulsi | G08B 21/06 340/575 |
| 8,362,882 | B2 * | 1/2013 | Heubel | G06F 1/163 340/407.1 |
| 8,390,439 | B2 * | 3/2013 | Cruz-Hernandez | A61B 5/02438 340/407.1 |
| 8,493,354 | B1 * | 7/2013 | Birnbaum | G06F 3/016 340/407.2 |

(Continued)

OTHER PUBLICATIONS

Any information that are not included with this Information Disclosure Statement can be found in U.S. Appl. No. 13/597,300.

*Primary Examiner* — Hoi Lau
(74) *Attorney, Agent, or Firm* — Miles & Stockbridge P.C.

(57) ABSTRACT

A haptic representation system is provided that generates a haptic effect in response to sensor input. The sensor input is mapped to a haptic signal. The haptic signal is sent to an actuator configured to receive the haptic signal. The actuator utilizes the haptic signal to generate the haptic effect.

20 Claims, 11 Drawing Sheets

(56) References Cited

U.S. PATENT DOCUMENTS

| | | | | |
|---|---|---|---|---|
| 8,570,161 B2* | 10/2013 | Ramsay | G06F 1/1626 | 340/407.1 |
| 8,570,296 B2* | 10/2013 | Birnbaum | G06F 3/016 | 340/407.2 |
| 8,711,118 B2* | 4/2014 | Short | G06F 3/016 | 340/407.2 |
| 8,866,774 B2* | 10/2014 | Leem | G06F 3/04886 | 340/407.1 |
| 9,116,546 B2* | 8/2015 | Birnbaum | G08B 6/00 | |
| 2005/0134561 A1* | 6/2005 | Tierling | G06F 3/016 | 345/156 |
| 2006/0066569 A1* | 3/2006 | Eid | G06F 3/016 | 345/156 |
| 2006/0103634 A1* | 5/2006 | Kim | G06F 3/016 | 345/173 |
| 2006/0284849 A1 | 12/2006 | Grant et al. | | |
| 2006/0288137 A1 | 12/2006 | Grant et al. | | |
| 2007/0057913 A1* | 3/2007 | Eid | G06F 3/016 | 345/156 |
| 2007/0139167 A1* | 6/2007 | Gilson | G06F 1/163 | 340/407.1 |
| 2008/0084298 A1* | 4/2008 | King | G08B 6/00 | 340/540 |
| 2009/0021473 A1* | 1/2009 | Grant | G06F 3/016 | 345/156 |
| 2009/0174672 A1* | 7/2009 | Schmidt | G06F 3/041 | 345/173 |
| 2009/0189746 A1* | 7/2009 | Ullrich | A61B 5/0002 | 340/407.1 |
| 2009/0231113 A1* | 9/2009 | Olien | G11B 31/00 | 340/407.2 |
| 2009/0267846 A1* | 10/2009 | Johnson | G08B 21/12 | 343/703 |
| 2010/0007474 A1* | 1/2010 | Behm | A61H 3/061 | 340/407.1 |
| 2010/0013653 A1* | 1/2010 | Birnbaum | G06F 1/1613 | 340/669 |
| 2010/0097228 A1* | 4/2010 | Schultz | G08B 25/10 | 340/600 |
| 2010/0123588 A1* | 5/2010 | Cruz Hernandez | A61B 5/02438 | 340/573.1 |
| 2010/0141407 A1* | 6/2010 | Heubel | G06F 1/163 | 340/407.1 |
| 2010/0253525 A1* | 10/2010 | Engel | G08B 6/00 | 340/573.1 |
| 2010/0277430 A1 | 11/2010 | Cruz-Hernandez et al. | | |
| 2010/0283588 A1* | 11/2010 | Gomez | G06F 3/016 | 340/407.2 |
| 2010/0283727 A1* | 11/2010 | Jiang | G06F 3/017 | 345/156 |
| 2010/0283731 A1* | 11/2010 | Grant | G06F 3/016 | 345/158 |
| 2011/0025480 A1* | 2/2011 | Hwang | H04M 19/047 | 340/407.1 |
| 2011/0102162 A1* | 5/2011 | Gregorio | G06F 3/016 | 340/407.2 |
| 2011/0121953 A1* | 5/2011 | Grant | A63F 13/02 | 340/407.1 |
| 2011/0128132 A1* | 6/2011 | Ullrich | G06F 3/16 | 340/407.1 |
| 2011/0128133 A1* | 6/2011 | Ullrich | A61B 5/0002 | 340/407.2 |
| 2011/0254672 A1* | 10/2011 | Ciesla | G06F 3/016 | 340/407.2 |
| 2012/0001749 A1* | 1/2012 | Cruz-Hernandez | A61B 5/02438 | 340/522 |
| 2012/0028577 A1* | 2/2012 | Rodriguez | H04N 21/44008 | 455/41.1 |
| 2012/0056733 A1* | 3/2012 | Ramsay | G06F 1/1626 | 340/407.2 |
| 2012/0068835 A1* | 3/2012 | Li | G06F 3/016 | 340/407.2 |
| 2012/0070805 A1* | 3/2012 | Wong | G09B 21/005 | 434/114 |
| 2012/0098789 A1* | 4/2012 | Ciesla | G06F 3/044 | 345/174 |
| 2012/0160967 A1* | 6/2012 | Scott | B64C 13/02 | 244/223 |
| 2012/0229400 A1* | 9/2012 | Birnbaum | G06F 3/016 | 345/173 |
| 2012/0235935 A1* | 9/2012 | Ciesla | G06F 3/0202 | 345/173 |
| 2012/0262305 A1* | 10/2012 | Woodard | G08G 1/147 | 340/932.2 |
| 2012/0265434 A1* | 10/2012 | Woodard | G08G 1/147 | 701/423 |
| 2012/0268412 A1* | 10/2012 | Cruz-Hernandez | G06F 3/0488 | 345/174 |
| 2012/0274470 A1* | 11/2012 | Sandvick | G01N 33/02 | 340/584 |
| 2012/0306632 A1* | 12/2012 | Fleizach | G06F 3/016 | 340/407.2 |
| 2012/0306790 A1* | 12/2012 | Kyung | G06F 3/016 | 345/173 |
| 2013/0207904 A1* | 8/2013 | Short | G06F 3/016 | 345/173 |
| 2013/0307786 A1* | 11/2013 | Heubel | G06F 3/016 | 345/173 |
| 2014/0055358 A1* | 2/2014 | Birnbaum | G06F 3/016 | 345/168 |
| 2014/0062682 A1* | 3/2014 | Birnbaum | G08B 6/00 | 340/407.2 |
| 2014/0132388 A1* | 5/2014 | Alalawi | G09B 21/003 | 340/4.12 |

\* cited by examiner

SYSTEM FOR HAPTICALLY REPRESENTING SENSOR INPUT

CROSS-REFERENCE TO RELATED APPLICATIONS

This application is a continuation application of U.S. patent application Ser. No. 13/597,300, filed on Aug. 29, 2012 (herein incorporated by reference).

FIELD

One embodiment is directed generally to a device, and more particularly, to a device that produces haptic effects.

BACKGROUND

Haptics is a tactile and force feedback technology that takes advantage of a user's sense of touch by applying haptic feedback effects (i.e., "haptic effects"), such as forces, vibrations, and deformations, to the user. A device, such as a mobile device, touchscreen device, and personal computer, can be configured to generate haptic effects in order to provide a more immersive experience for the user. For example, when a user interacts with the device using, for example, a button, touchscreen, lever, joystick, wheel, or some other control, a haptic signal can be generated, where the haptic signal causes the device to produce an appropriate haptic effect. The user can experience the haptic effect, and the user's interaction with the device can be enhanced.

SUMMARY

One embodiment is a haptic representation system that generates a haptic effect. The system receives input from a sensor. The system maps the received input to a haptic signal. The system further sends the haptic signal to an actuator to generate the haptic effect.

BRIEF DESCRIPTION OF THE DRAWINGS

Further embodiments, details, advantages, and modifications will become apparent from the following detailed description of the preferred embodiments, which is to be taken in conjunction with the accompanying drawings.

DETAILED DESCRIPTION

One embodiment is a haptic representation system that can produce a haptic effect that represents input that is generated by a sensor and received by the haptic representation system. In certain embodiments, the received input includes extra-sensory information, where extra-sensory information is information that cannot normally be perceived by a human being, such as an electromagnetic field, infra-red light, ultraviolet light, radiation, or subtle changes in temperature. In some embodiments, the haptic effect is a deformation haptic effect produced by a deformation actuator, where a deformation haptic effect includes an alteration of a shape and/or size of a component operably coupled to the deformation actuator. In certain embodiments, the deformation haptic effect that is produced by the deformation actuator is generated based on the extra-sensory information included in the received input generated by the sensor.

As described below in greater detail, a "vibration effect" or "vibration haptic effect" is an effect that produces a vibration. A "vibration actuator" is an actuator configured to produce a vibration haptic effect. A "force effect" or "force haptic effect" is an effect that produces a force. A "force actuator" is an actuator configured to produce a force haptic effect. A "deformation effect" or "deformation haptic effect" is an effect that deforms a structure or shape. A "deformation actuator" is an actuator configured to produce a deformation haptic effect. An "impedance effect" or "impedance haptic effect" is an effect that produces resistance or opposition to an applied force. An "impedance actuator" is an actuator configured to produce an impedance haptic effect.

Figure 1:
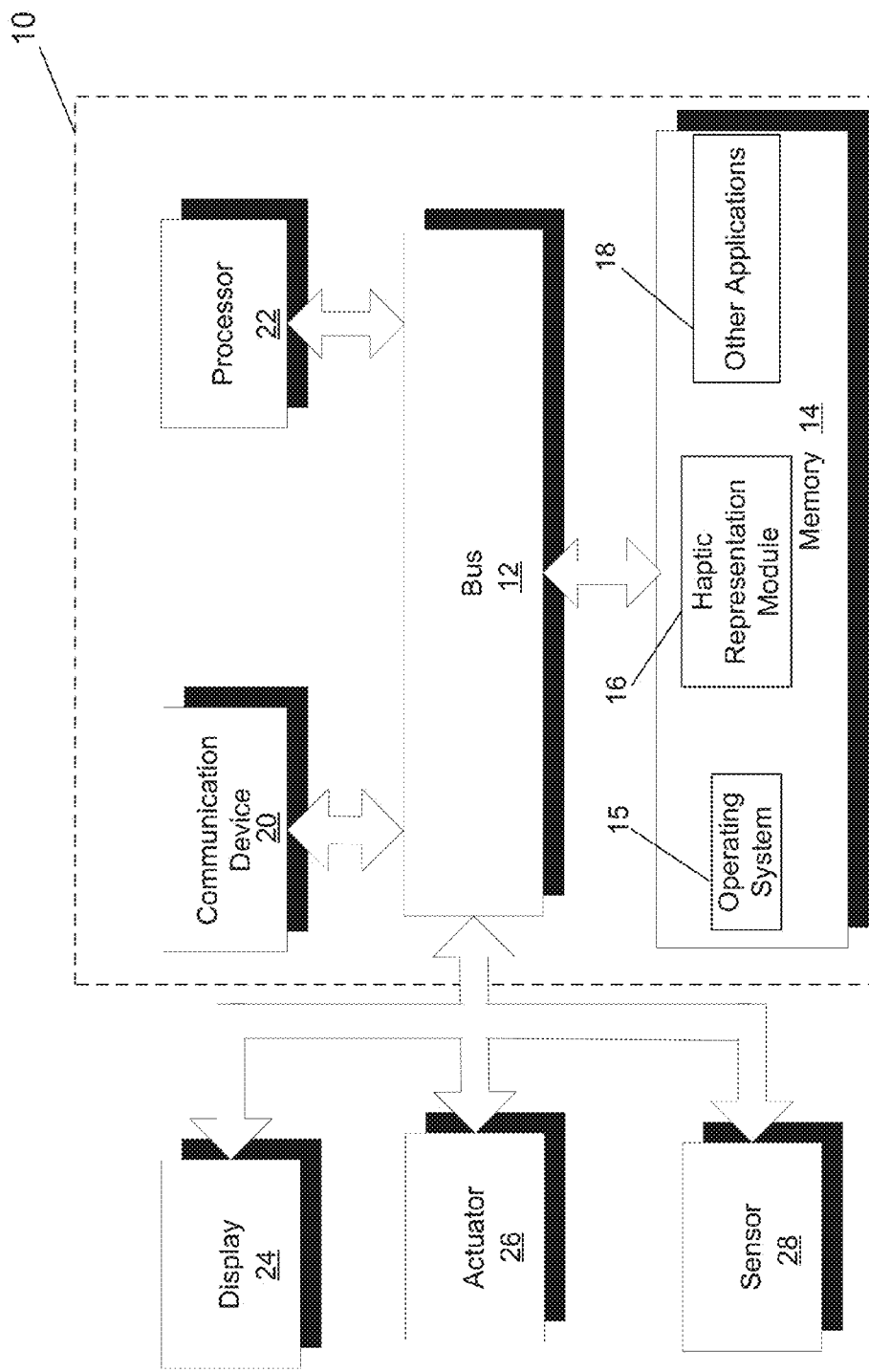
FIG. 1 illustrates a block diagram of a haptic representation system in accordance with one embodiment of the invention.

FIG. 1 illustrates a block diagram of a haptic representation system 10 in accordance with one embodiment of the invention. In one embodiment, system 10 is part of a device (such as device 200 illustrated in FIG. 2, where device 200 is described below in greater detail), and system 10 provides a haptic representation functionality for the device. Although shown as a single system, the functionality of system 10 can be implemented as a distributed system. System 10 includes a bus 12 or other communication mechanism for communicating information, and a processor 22 coupled to bus 12 for processing information. Processor 22 may be any type of general or specific purpose processor. System 10 further includes a memory 14 for storing information and instructions to be executed by processor 22. Memory 14 can be comprised of any combination of random access memory ("RAM"), read only memory ("ROM"), static storage such as a magnetic or optical disk, or any other type of computer-readable medium.

A computer-readable medium may be any available medium that can be accessed by processor 22 and may include both a volatile and nonvolatile medium, a removable and non-removable medium, a communication medium, and a storage medium. A communication medium may include computer readable instructions, data structures, program modules or other data in a modulated data signal such as a carrier wave or other transport mechanism, and may include any other form of an information delivery medium known in the art. A storage medium may include RAM, flash memory, ROM, erasable programmable read-only memory ("EPROM"), electrically erasable programmable read-only memory ("EEPROM"), registers, hard disk, a removable disk, a compact disk read-only memory ("CD-ROM"), or any other form of a storage medium known in the art.

In one embodiment, memory 14 stores software modules that provide functionality when executed by processor 22. The modules include an operating system 15 that provides operating system functionality for system 10, as well as the rest of a device in one embodiment. The modules further include a haptic representation module 16 that generates a haptic effect that represents received input, as disclosed in more detail below. In certain embodiments, haptic representation module 16 can comprise a plurality of modules, where each individual module provides specific individual functionality for generating a haptic effect that represents received input. System 10 will typically include one or more additional application modules 18 to include additional functionality, such as the Integrator® Haptic Development Platform by Immersion Corporation.

System 10, in embodiments that transmit and/or receive data from remote sources, further includes a communication device 20, such as a network interface card, to provide mobile wireless network communication, such as infrared, radio, Wi-Fi, or cellular network communication. In other embodiments, communication device 20 provides a wired network connection, such as an Ethernet connection or a modem.

Processor 22 is further coupled via bus 12 to a display 24, such as a Liquid Crystal Display ("LCD"), for displaying a graphical representation or user interface to a user. The display 24 may be a touch-sensitive input device, such as a touchscreen, configured to send and receive signals from processor 22, and may be a multi-touch touchscreen.

System 10, in one embodiment, further includes an actuator 26. Processor 22 may transmit a haptic signal associated with a generated haptic effect to actuator 26, which in turn outputs haptic effects, such as vibrotactile haptic effects and deformation haptic effects. Actuator 26 includes an actuator drive circuit. Actuator 26 may be, for example, an electric motor, an electro-magnetic actuator, a voice coil, a shape memory alloy, an electro-active polymer, a solenoid, an eccentric rotating mass motor ("ERM"), a linear resonant actuator ("LRA"), a piezoelectric actuator, a high bandwidth actuator, an electroactive polymer ("EAP") actuator, an electrostatic friction display, or an ultrasonic vibration generator. In alternate embodiments, system 10 can include one or more additional actuators, in addition to actuator 26 (not illustrated in FIG. 1). In other embodiments, a separate device from system 10 includes an actuator that generates the haptic effects, and system 10 sends generated haptic effect signals to that device through communication device 20.

System 10, in one embodiment, further includes a sensor 28. Sensor 28 can be configured to detect a form of energy, or other physical property, such as, but not limited to, acceleration, bio signals, distance, flow, force/pressure/strain/bend, humidity, linear position, orientation/inclination, radio frequency, rotary position, rotary velocity, manipulation of a switch, temperature, vibration, or visible light intensity. Sensor 28 can further be configured to convert the detected energy, or other physical property, into an electrical signal, or any signal that represents virtual sensor information. Sensor 28 can be any device, such as, but not limited to, an accelerometer, an electrocardiogram, an electroencephalogram, an electromyograph, an electrooculogram, an electropalatograph, a galvanic skin response sensor, a capacitive sensor, a hall effect sensor, an infrared sensor, an ultrasonic sensor, a pressure sensor, a fiber optic sensor, a flexion sensor (or bend sensor), a force-sensitive resistor, a load cell, a LuSense CPS$^2$ 155, a miniature pressure transducer, a piezo sensor, a strain gage, a hygrometer, a linear position touch sensor, a linear potentiometer (or slider), a linear variable differential transformer, a compass, an inclinometer, a magnetic tag (or radio frequency identification tag), a rotary encoder, a rotary potentiometer, a gyroscope, an on-off switch, a temperature sensor (such as a thermometer, thermocouple, resistance temperature detector, thermistor, or temperature-transducing integrated circuit), microphone, photometer, altimeter, bio monitor, or a light-dependent resistor.

Figure 2:
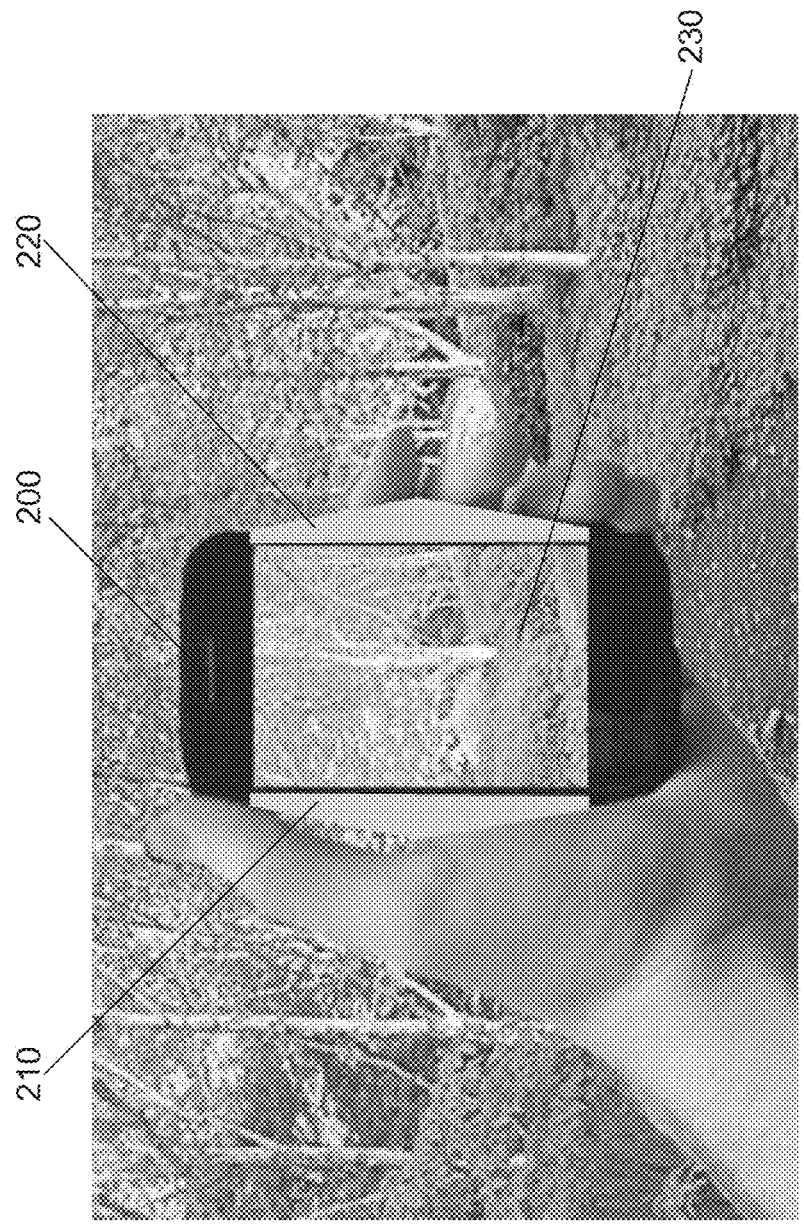
FIG. 2 illustrates an example of a device with sensor input and haptic output, according to one embodiment of the invention.

FIG. 2 illustrates an example of a device 200 with sensor input and haptic output, according to one embodiment of the invention. As previously described, in one embodiment, device 200 can include a haptic representation system (such as haptic representation system 10 illustrated in FIG. 1) that can represent the sensor input as haptic output. According to the embodiment, device 200 is a mobile device that can be carried within a user's hand. Device 200 can include a sensor (such as sensor 28 of FIG. 1), where the sensor not illustrated in FIG. 2, extensions 210 and 220, and display 230. The sensor can be configured to detect sensory information and extra-sensory information, where sensory information is information that can normally be perceived by a human being, and where extra-sensory information is information that cannot normally be perceived by a human being. The sensor can be further configured to produce sensor input based on the detected information. Extensions 210 and 220 can each be coupled to an actuator (not illustrated in FIG. 2). The actuator can be a vibration actuator or a deformation actuator. A vibration actuator can cause extensions 210 and 220 to vibrate based on the sensor input produced by the sensor. A deformation actuator can cause extensions 210 and 220 to deform based on the sensor input produced by the sensor. The specifics of a vibration actuator and a deformation actuator are further described in greater detail. Display 230 can display visual information based on the sensor input produced by the sensor.

Figure 3:
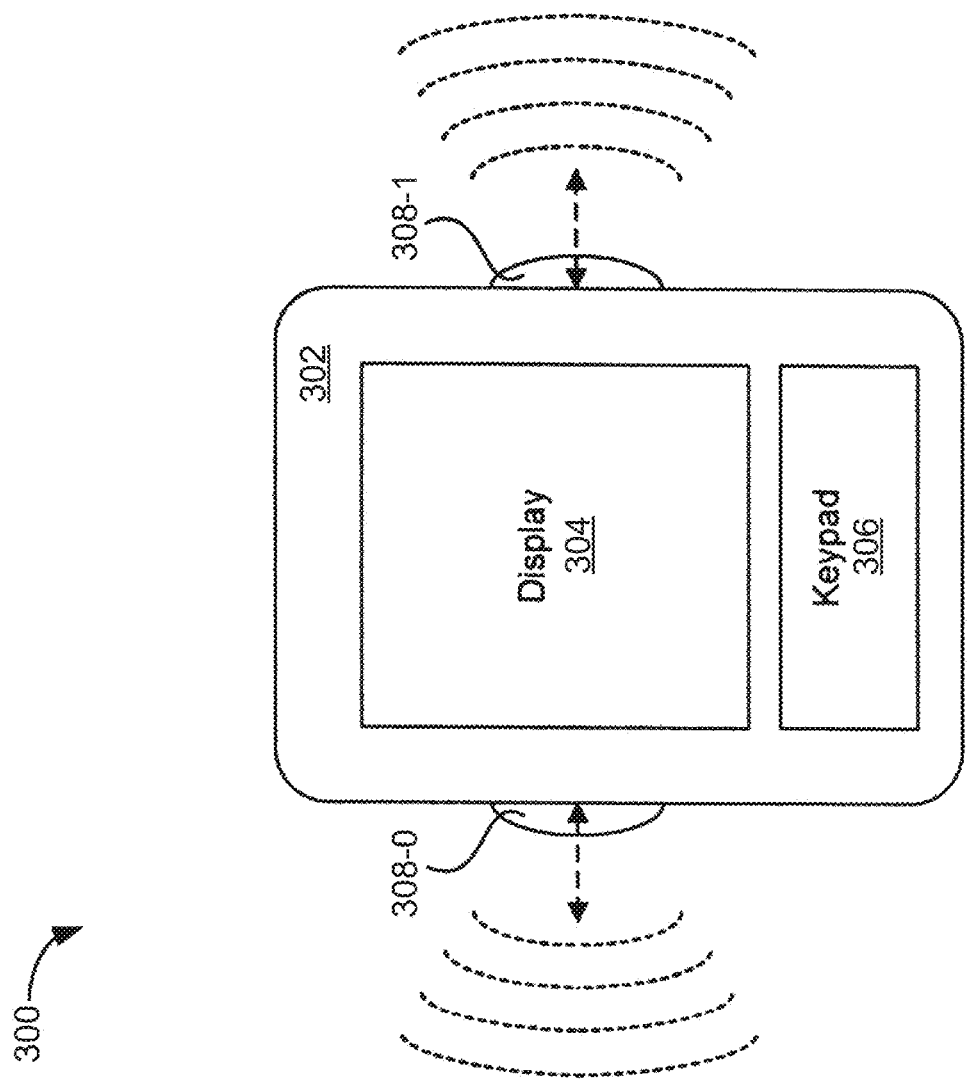
FIG. 3 illustrates a block diagram of a device capable of providing vibrotactile effects and/or kinesthetic effects, according to one embodiment of the invention.

FIG. 3 illustrates a block diagram of a device 300 capable of providing vibrotactile effects (also identified as "vibration haptic effects") and/or kinesthetic effects (also identified as "deformation haptic effects"), according to one embodiment of the invention. Device 300 includes a housing 302, a display 304, a keypad 306, and extensions 308-0 and 308-1. In another embodiment, keypad 306 is part of a touchscreen display 304. Device 300, in one embodiment, is a wireless portable system capable of providing wireless audio/video communication, mobile data communication, a remote game console, and the like. For example, device 300 may be a cellular phone, a PDA, a smart phone, a laptop computer, a game console, and/or a handheld electronic device capable of processing information as well as providing haptic feedback.

To provide a haptic feedback to a user's hand in accordance with an operation mode, device 300 is capable of macroscopically altering its outer enclosure or housing 302

(which includes extensions 308) in response to the nature of the application. Depending on the application, extensions 308 can expand or contract (as indicated by arrows in FIG. 3) thereby macroscopically altering the shape and/or size of housing 302. In one embodiment, a shape is "macroscopically" altered if it changes to the extent that the change can be detected by the user via, for example, sight or feel. For example, a cell phone or smart phone device capable of changing its outer enclosure shape ("shape changing device") may be used to emulate a handshake between two users. To convey a handshake, a first user, for instance, might squeeze its first shape changing device to cause a pulse or squeeze of a second shape changing device of a second user, where the first and second users are engaged in a communication, such as a telephone call, via the first and second shape changing devices connected to the first shape changing device. In other words, a shape input or shape signal is sent from the first shape changing device to a second shape changing device indicating that the second device should activate its haptic mechanism to change its shape for emulating a handshake. In other embodiments, additional portions of device 300 besides housing 302 may also change shape, such as display 304, or input elements such as keypad 306.

Systems such as device 300 may employ vibrotactile effects (also identified as vibration haptic effects) and/or kinesthetic effects (also identified as deformation haptic effects) to emulate shape changing effects. Vibrotactile effects, for instance, may be used to incorporate haptic feedback to a user via a handheld device. Such haptic feedback effects may be characterized by relatively high-frequency (e.g., about 160-220 Hz) and relatively small displacement (e.g., about 50-500 micrometers) vibrations. Further, different types of haptic information such as confirmation of button clicks and alerts can also be conveyed. Kinesthetic effects, on the other hand, may be characterized by relatively large displacements (e.g., about 1-10 mm) and relatively low-frequency (e.g., about 0-40 Hz) motions. Deformable or flexible surfaces can be used for effective emulation of kinesthetic effects, such as macroscopically changing surface properties depending on the application or activated feature.

Kinesthetic effects may be effectively emulated using deformable haptic surfaces. For example, kinesthetic effects may allow a handheld device to be used as a directional navigation tool. In this example, activation of deformable surfaces at different locations on the handheld device can be used as a haptic display of directional information. In another example, kinesthetic effects allow performance of specific effects (e.g., pulsation, heartbeat, etc.), which could be of value in virtual tele-presence and/or social networking applications. In one example, a heartbeat of one person can be emulated by expanding and contracting deformable pads on the sides of a cell phone of another person connected via a telephone call. In another example, a squeezing of a cell phone at one end of a call can be emulated as a handshake sensation at another cell phone at the other end of the call.

Force haptic effects or "force effects" may be emulated using various types of input signals to drive a haptic actuator, such as, but not limited to, an ERM. Certain types of input signals may be used to provide various impulse force effects or a "jerk sensation" as opposed to more constant force effects (e.g., pushing or pulling force effects). In one example, such impulse force effects may simulate being poked by a finger. In one example, such impulse force effects may simulate a strike, for example, of a golf club impacting a golf ball. In one example, such impulse force effects may simulate a racket impacting a tennis ball. Impulse force effects may be used to simulate other gaming environments.

Device 300, in one embodiment, is able to change shape based on an operating mode (e.g., application, activated feature, etc.), as opposed to merely being manipulated by a user. Various haptic materials and/or actuators can be used in the haptic mechanism to cause varying shapes in a flexible surface of device 300. For example, EAPs may be used to form one or more actuators in the haptic mechanism for shape changing based on activation of control signals. In other embodiments, a piezoelectric element, programmable gels, or a fiber of shape memory alloys ("SMAs") can be used as actuators.

In one embodiment, indications of a device operating mode such as an activated feature and application can activate predetermined patterns of a haptic mechanism. Such patterns can then be applied to the flexible surface of device 300 using a deformation mechanism. A haptic substrate that includes a plurality of actuators can be applied to the surface to enact or form the patterns. EAPs, for example, can be employed to form one or more actuators in a haptic mechanism such that activating signals received by the haptic mechanism can convey flexible surface shapes. The haptic substrate can be formed from micro-electro-mechanical systems ("MEMS") elements, thermal fluid pockets, MEMS pumps, resonant devices, variable porosity membranes, laminar flow modulation, etc.

Extensions 308 can be controllable as to displacement, as well as any pulsation or other suitable effects and/or patterns. For example, one user can squeeze a first device, and a second device connected on a call to the first device can pulse or squeeze in the hand of a second user to convey a physical handshake. Thus, a signal can be sent from the first device to the second device to indicate that the second device should change shape to emulate a handshake (e.g., a low frequency force or pressure like a squeeze of a hand). In this fashion, any predetermined shape change characteristics or patterns supportable by the underlying haptic mechanism, substrate, and/or actuator control can be employed.

Further details of devices capable of producing shape changing or deformation haptic effects are described in U.S. patent application Ser. No. 12/776,121, filed on May 7, 2010, herein incorporated by reference.

Figure 4:
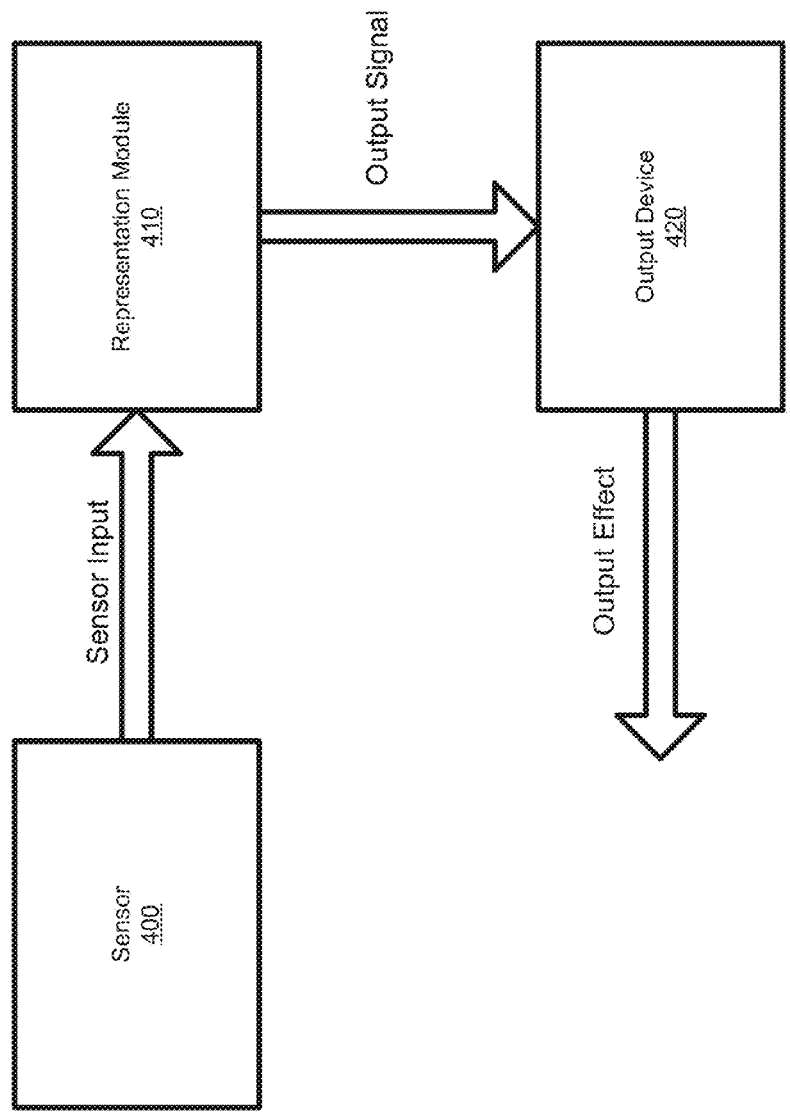
FIG. 4 illustrates a diagram of an example mapping of sensor input to an output signal that, when played at an output device, produces an output effect, according to one embodiment of the invention.

FIG. 4 illustrates a diagram of an example mapping of sensor input to an output signal that, when played at an output device, produces an output effect, according to one embodiment of the invention. More specifically, FIG. 4 illustrates sensor 400. Sensor 400 can be identical to sensor 28 of FIG. 1. Sensor 400 can be a sensor configured to detect information. In certain embodiments, sensor 400 can be a sensor configured to detect extra-sensory information, where extra-sensory information is information that cannot normally be perceived by a human being. For example, in one embodiment, sensor 400 can be a magnetometer configured to detect electromagnetic fields. In another embodiment, sensor 400 can be a light sensor configured to detect light frequencies that are out of range of the human eye, such as an infra-red light frequency. In another embodiment, sensor 400 can be a temperature sensor configured to detect a change in temperature, even when the temperature change could not normally be detected by a human being. Based on the detected extra-sensory information, the sensor can generate sensor input, where the sensor input represents the detected extra-sensory information. In other embodiments, sensor 400 can be a sensor configured to detect sensory information, where sensory information is information that can normally be perceived by a human being.

FIG. 4 also illustrates representation module 410. When executed by a processor (not illustrated in FIG. 4), representation module 410 can receive the sensor input from sensor 400, map the sensor input to an output signal, and send the output signal to output device 420. According to the embodiment, representation module 410 can include an algorithm that maps the sensor input to an output signal, where the output signal is configured to produce an output effect when played at output device 420. Thus, in certain embodiments, representation module 410 can represent the extra-sensory information detected by sensor 400 (and which cannot normally be perceived by a human being) as an output effect that can be played at output device 420 (and thus, can be perceived by a human being). In this manner, representation module 410 can allow a human being to perceive extra-sensory information detected by sensor 400, which normally could not be perceived. In other embodiments, representation module 410 can also represent the sensory information detected by sensor 400 as an output effect that can be played at output device 420. In this manner, representation module 410 can augment a human being's normal perception of the sensory information detected by sensor 400.

In certain embodiments, representation module 410 can be a haptic representation module, such as haptic representation module 16 of FIG. 1. In these embodiments, when executed by a processor, representation module 410 can receive the sensor input from sensor 400, map the sensor input to a haptic signal, and send the haptic signal to output device 420, where output device 420 is an actuator, such as actuator 26 of FIG. 1. According to the embodiment, representation module 410 can include an algorithm that maps the sensor input to a haptic signal, where the haptic signal is configured to produce a haptic effect when played at output device 420. Thus, representation module 410 can represent the extra-sensory information detected by sensor 400 (and which cannot normally be perceived by a human being) as a haptic effect that can be played at output device 420 (and thus, can be perceived by a human being).

For example, in an embodiment where sensor 400 is a magnetometer, representation module 410 can map the input from the magnetometer into a deformation haptic signal or a vibration haptic signal for an actuator. A deformation haptic signal can be played at an actuator to generate a deformation haptic effect. A vibration haptic signal can be played at an actuator to generate a vibration haptic effect. As another example, in an embodiment where sensor 400 is a light sensor, representation module 410 can map the input from the light sensor into a video signal that can be displayed on a display screen, or an audio signal that can be played at a speaker. As yet another example, in an embodiment where sensor 400 is a radiation sensor, representation module 410 can map the input from the radiation sensor into either a deformation haptic signal or a vibration haptic signal for an actuator.

In certain embodiments, sensor 400 can be local to representation module 410 (i.e., sensor 400 and representation module 410 can be located within a single device). In other embodiments, sensor 400 is located on a separate device from representation module 410, and the sensor input is sent to representation module 410 over a network.

In certain embodiments, the mapping performed at representation module 410 includes determining whether the received sensor input exceeds a specified threshold (i.e., "specified value"). If the received sensor input exceeds the specified value, a corresponding output signal (such as a haptic signal) is generated, and the received sensor input is mapped to the generated output signal. If the received sensor input does not exceed the specified value, no output signal is generated.

In alternate embodiments, the mapping performed at representation module 410 includes mathematically transforming the received sensor input into a corresponding output signal (such as a haptic signal). This can be done continuously as sensor input is received, and thus, the corresponding output signal can be continuously modulated. As the output signal is continuously modulated, the corresponding output effect (such as a haptic effect) that is generated can also be continuously modulated.

FIG. 4 also illustrates output device 420. Output device 420 can receive the output signal sent by representation module 410, and can generate an output effect based on the output signal. In certain embodiments, output device 420 can be an actuator, such as actuator 26 of FIG. 1. In some of these embodiments, output device 420 can be a vibration actuator configured to produce vibration haptic effects. In other embodiments, output device 420 can be a deformation actuator configured to produce deformation haptic effects. In these embodiments, output device 420 can receive a haptic signal sent by representation module 410, and can generate a haptic effect based on the output signal. In embodiments where the haptic signal is a vibration haptic signal, output device 420 can produce a vibration haptic effect. In embodiments where the haptic signal is a deformation haptic signal, output device 420 can produce a deformation haptic effect. In other embodiments, output device 420 can be an output device configured to produce video effects, such as a display screen, or an output device configured to produce audio effects, such as a speaker.

For example, in an embodiment where sensor 400 is a magnetometer, and output device 420 is an actuator (such as a vibration actuator or a deformation actuator), output device 420 can deform and/or vibrate according to a presence of an electromagnetic field, the intensity of the electromagnetic field, or other attributes of the electromagnetic field. More specifically, sensor 400 can detect the electromagnetic field and produce sensor input based on one or more attributes of the electromagnetic field. Representation module 410 can map the sensor input produced by sensor 400 to a vibration haptic signal, a deformation haptic signal, or a combination therein. Based on the vibration haptic signal, the deformation haptic signal, or the combination therein, output device 420 can produce a vibration haptic effect (by vibrating), a deformation haptic effect (by deforming), or a combination therein.

As another example, in an embodiment where sensor 400 is a light sensor, and output device 420 is a display screen, output device 420 can display a visual representation based on the detection of infra-red light (or ultraviolet light). More specifically, sensor 400 can detect the infra-red light (or ultraviolet light) and produce senor input based one or more attributes of the infra-red light (or ultraviolet light). Representation module 410 can map the sensor input produced by sensor 400 to a video signal. Based on the video signal, output device 420 can produce a video effect (e.g., a visual representation of the detected light). In an alternate embodiment, output device 420 can be an actuator rather than a display screen. In this embodiment, representation module 410 can map the sensor input produced by sensor 400 to a vibration haptic signal or a deformation haptic signal. Based on the vibration haptic signal, or the deformation haptic signal, output device can produce a vibration haptic effect, or a deformation haptic effect, that represents the detected light. For example, if sensor 400 detects a significant amount of infra-red light, output device 420 can deform an amount that reflects the amount of detected infra-red light.

Thus, according to certain embodiments, a user's senses can be augmented, as the user can perceive attributes of an environment that would normally be difficult or impossible to perceive.

Figure 5:
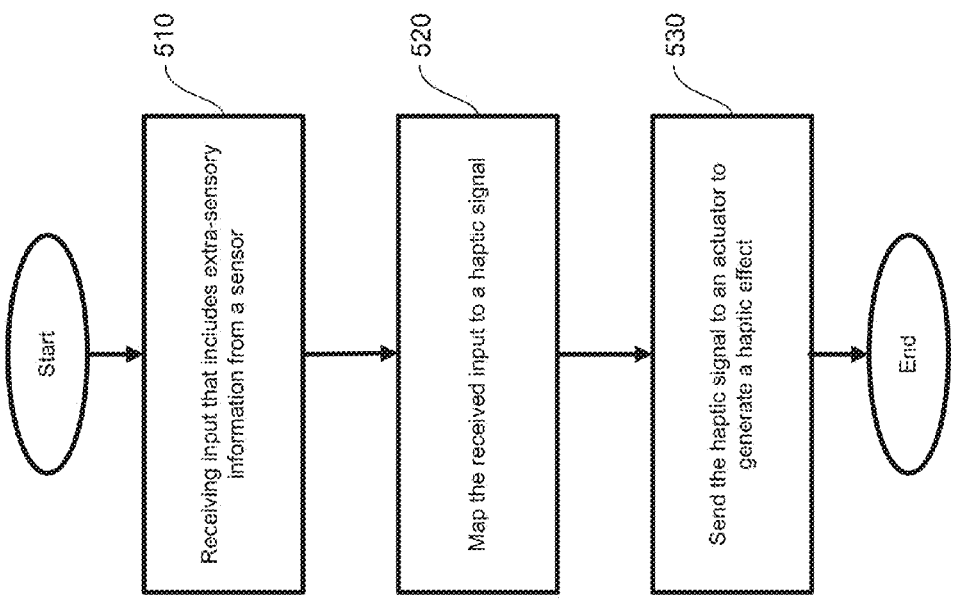
FIG. 5 illustrates a flow diagram of the functionality of a haptic representation module, according to one embodiment of the invention.

FIG. 5 illustrates a flow diagram of the functionality of a haptic representation module (such as haptic representation module 16 of FIG. 1), according to one embodiment of the invention. In one embodiment, the functionality of FIG. 5, as well as the functionality of FIG. 11, which is described below in greater detail, is implemented by software stored in memory or another computer-readable or tangible medium, and executed by a processor. In other embodiments, the functionality may be performed by hardware (e.g., through the use of an application specific integrated circuit ("ASIC"), a programmable gate array ("PGA"), a field programmable gate array ("FPGA"), etc.), or any combination of hardware and software. Furthermore, in alternate embodiments, the functionality may be performed by hardware using analog components.

The flow begins and proceeds to 510. At 510, input is received from a sensor. The input can include extra-sensory information, where extra-sensory information is information that cannot normally be perceived by a human being. In certain embodiments, the input can include one or more interaction parameters, where each interaction parameter can include a value. In certain embodiments, the sensor can be a magnetometer configured to generate the input based on an electromagnetic field that the magnetometer detects. In other embodiments, the sensor can be a light sensor configured to generate the input based on energy that the light sensor detects. The energy can include ultraviolet light. Alternately, the energy can include infra-red light. In other embodiments, the sensor can be a radiation sensor configured to generate the input based on radiation that the radiation sensor detector. The flow proceeds to 520.

At 520, the received input is mapped to a haptic signal. In certain embodiments, the mapping the received input to the haptic signal includes generating the haptic signal when the value of at least one interaction parameter exceeds a specified value. In other embodiments, the mapping the received input to the haptic signal includes continuously modulating the haptic signal based on a continuous updating of the value of at least one interaction parameter. The flow proceeds to 530.

At 530, the haptic signal is sent to an actuator to generate a haptic effect. In certain embodiments, the actuator is a vibration actuator, and the haptic effect generated by the vibration actuator is a vibration haptic effect. In other embodiments, the actuator is a deformation actuator, and the haptic effect generated by the deformation actuator is a deformation haptic effect. The flow then ends.

In certain embodiments, a haptic device can output various types of information based on sensor input. Examples include: outputting haptic effects based on input from a magnetometer; outputting deformation haptic effects on a display of the device to create a "geofence"; augmenting sensory perception by outputting deformation haptic effects; enhancing normal sensory perception by outputting deformation haptic effects; and outputting haptic effects based on either a user's mood, ambient awareness, or bio feedback.

Furthermore, in certain embodiments, a deformation actuator of a haptic device can output deformation haptic effects using one of a plurality of interaction modes. Examples of the interaction modes include: applying pressure to the body of a user; changing shape (where the shape-change can include a change in a macro-shape of the haptic device or a change in a texture of the haptic device); and outputting an impedance haptic effect (where the haptic device assesses user input and outputs one or more haptic effects based on the user input).

Figure 6:
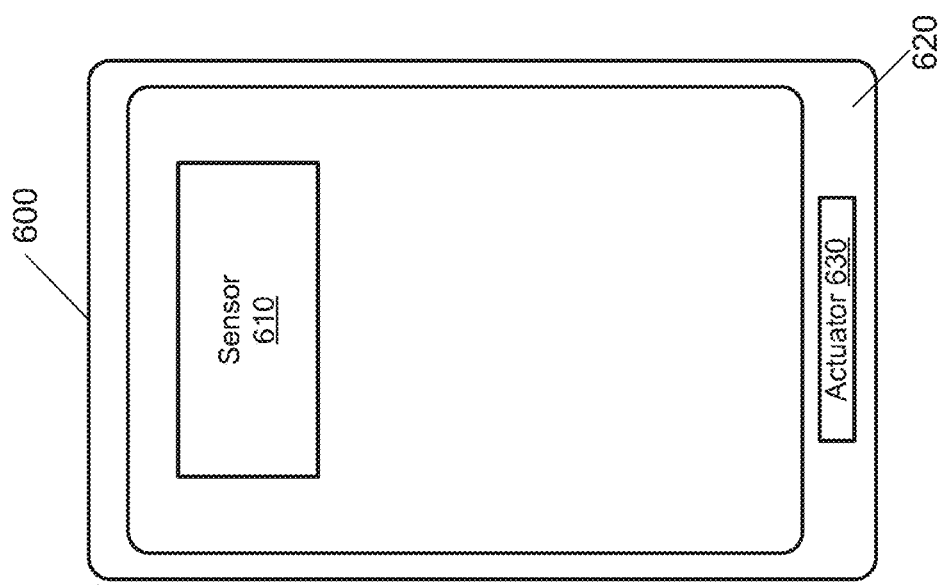
FIG. 6 illustrates a block diagram of a device capable of producing a haptic effect to augment sensory perception, according to one embodiment of the invention.

FIG. 6 illustrates a block diagram of a device 600 capable of producing a haptic effect to augment sensory perception, according to one embodiment of the invention. Device 600 can include sensor 610. Sensor 610 can be identical to sensor 28 of FIG. 1. Sensor 610 can be a sensor configured to detect information. Based on the detected information, the sensor can generate sensor input, where the sensor input represents the detected information. In certain embodiments, sensor 610 can be a sensor configured to detect extra-sensory information, where extra-sensory information is information that cannot normally be perceived by a human being.

Device 600 can further include a housing 620. Housing 620, also identified as an outer enclosure of device 600, can be operatively coupled to an actuator 630. Housing 620 can also include a haptic surface which overlays at least a portion of housing 620. In certain embodiments, the haptic surface can be configured to apply a force in response to a force haptic effect produced by actuator 630. In these embodiments, actuator 630 can be a force actuator that can be configured to produce a force haptic effect. In other certain embodiments, the haptic surface can be configured to macroscopically alter its physical shape in response to a deformation haptic effect produced by actuator 630. In these embodiments, actuator 630 can be a deformation actuator that can be configured to produce a deformation haptic effect. In other certain embodiments, the haptic surface can be configured to produce a mechanical impedance in response to an impedance haptic effect produced by actuator 630. In these embodiments, actuator 630 can be an impedance actuator that can be configured to produce an impedance haptic effect. Thus, in certain embodiments, actuator 630 can cause housing 620 of device 600 to reflect the information detected by sensor 610, including the extra-sensory information detected by sensor 610.

In one embodiment, sensor 610 can be a sensor configured to detect a barometric pressure, and actuator 630 can cause housing 620 to apply a force, to deform, or to produce a mechanical impedance based on the detected barometric pressure. Thus, in this embodiment, device 600 can indicate possible imminent changes in weather patterns due to an increase or decrease in detected barometric pressure. In another embodiment, sensor 610 can be a magnetometer configured to detect an electromagnetic field, and actuator 630 can cause housing 620 to apply a force, to deform, or to produce a mechanical impedance based on one or more properties of the detected electromagnetic field, such as the presence of the electromagnetic field, the intensity of the electromagnetic field, or the periodicity of the electromagnetic field. For example, a user could hold device 600 near an electrical cord to determine whether the electrical cord is connected to a power source in response to housing 620 of device 600 applying a force, applying a deformation, or producing a mechanical impedance in the presence of an alternating electromagnetic field surrounding the cord.

In another embodiment, sensor 610 can be a radiation sensor configured to detect radiation, and actuator 630 can cause housing 620 to apply a force, to deform, or to produce a mechanical impedance based on the detected radiation. For example, device 600 can detect a level of ambient radiation within an environment using sensor 610, and actuator 630 can cause housing 620 to apply a force, to deform, or to produce a mechanical impedance based on the detected level of ambient radiation. In another embodiments, sensor 610 can be a sensor configured to detect a signal sent by a global positioning system ("GPS"), where the signal can represent a position of device 600, and actuator 630 can cause housing 620 to apply a force, to deform, or to produce a mechanical impedance based on the detected signal (i.e., the detected position of device 600). Thus, device 600 can create a geofence (i.e., a virtual perimeter for a real-world geographical area).

In another embodiment, sensor 610 can be a galvanic skin response sensor configured to detect an electrical conductance of the skin of a user, and actuator 630 can cause housing 620 to apply a force, to deform, or to produce a mechanical impedance based on characteristics of the user identified from the detected electrical conductance of the skin of the user, such as mood, ambient awareness, and bio feedback. Thus, device 600 can apply a force, deform, or produce a mechanical impedance in order to mirror an identified state of the user.

Figure 7:
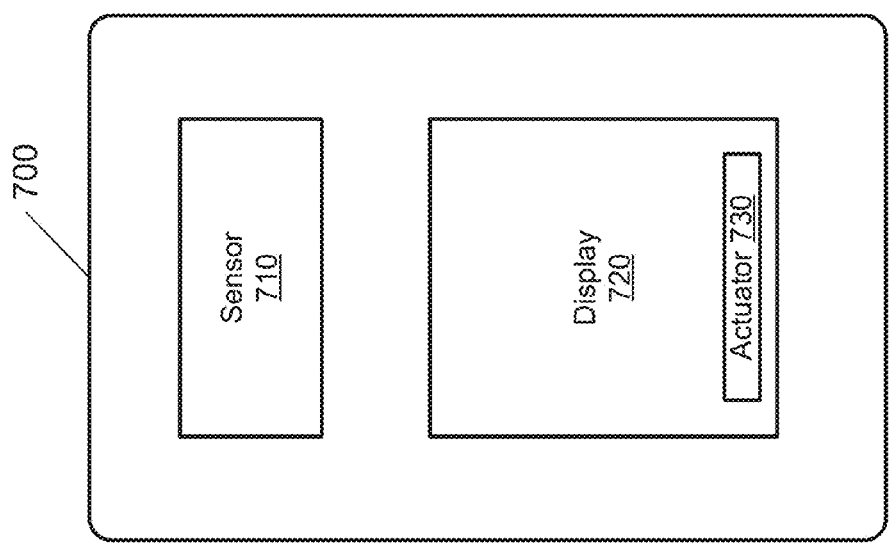
FIG. 7 illustrates a block diagram of a device capable of producing a haptic effect to augment visual information displayed within a display screen, according to one embodiment of the invention.

FIG. 7 illustrates a block diagram of a device 700 capable of producing a haptic effect to augment visual information displayed within a display screen, according to one embodiment of the invention. Device 700 can include sensor 710. Sensor 710 can be identical to sensor 28 of FIG. 1. Sensor 710 can be a sensor configured to detect information. Based on the detected information, the sensor can generate sensor input, where the sensor input represents the detected information. In certain embodiments, sensor 710 can be a sensor configured to detect extra-sensory information, where extra-sensory information is information that cannot normally be perceived by a human being. Device 700 can further include a display 720. Display 720 can be configured to display a visual image. Display 720 can be operatively coupled to an actuator 730. Display 720 can be configured to macroscopically alter its physical shape in response to a deformation haptic output effect produced by actuator 730. In certain embodiments, actuator 730 can be a deformation actuator that can be configured to produce a deformation haptic effect. Thus, in these embodiments, device 700 can be configured to overlay a visual image displayed within display 720 with a deformation of at least a portion of a screen of display 720, where the deformation is produced by actuator 730 and based on information detected by sensor 710. For example, display 720 can display a scene, and can further display invisible features of the scene as screen surface features/deformations within display 720. Thus, the visual scene displayed within 720 is generally not changed from how it actually looks.

In one embodiment, sensor 710 can be a light sensor configured to detect light frequencies, including light frequencies that are within a range of the human eye, and also including light frequencies that are out of range of the human eye, and sensor 710 can be configured to capture a full-spectrum photograph of a scene. According to the embodiment, a visual image that represents the light frequencies that are within a range of the human eye can be displayed within display 720, and a deformation of at least a portion of a screen of display 720 that represents the light frequencies that are out of range of the human eye can be produced, where the deformation is produced by actuator 730 and based on information detected by sensor 710. Thus, the visual image that is displayed within display 720 is preserved, but the light frequencies that are out of range of the human eye detected by sensor 710 can be perceived by the user.

Figure 8:
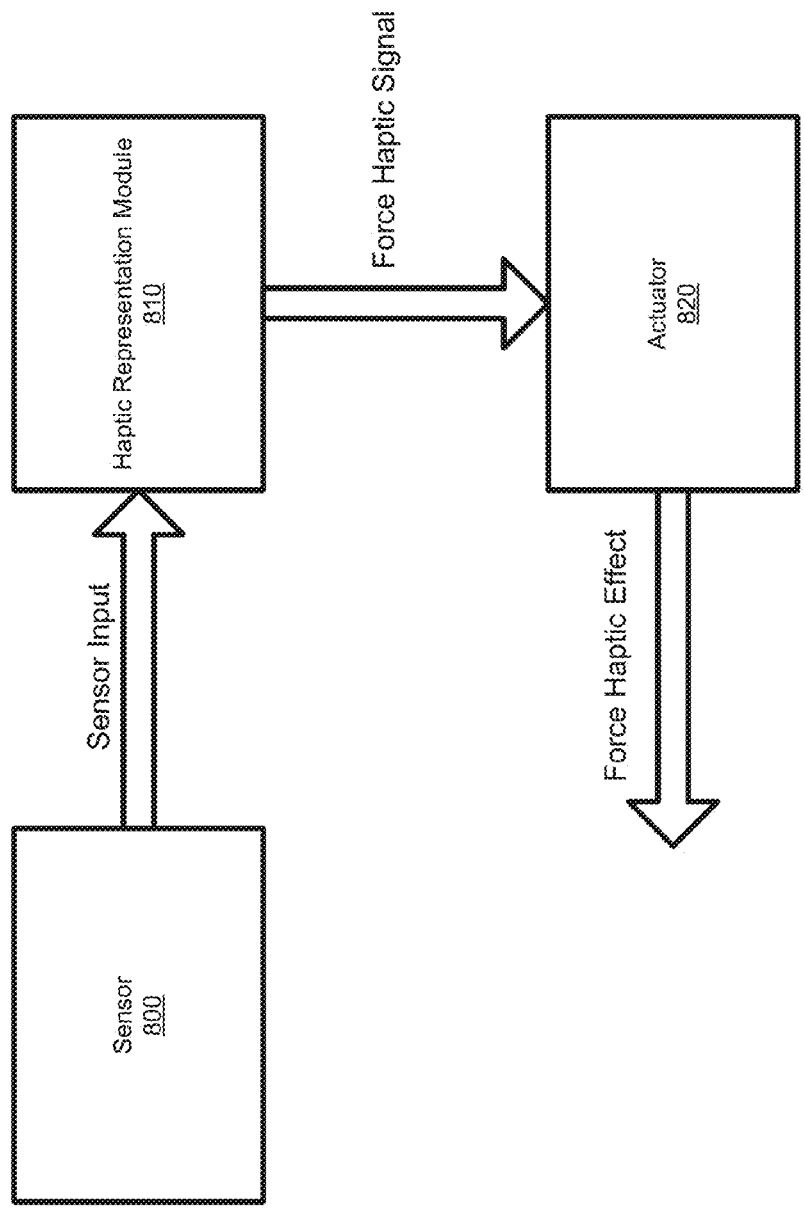
FIG. 8 illustrates a diagram of an example mapping of sensor input to a force haptic signal that, when played at an actuator, produces a force haptic effect, according to one embodiment of the invention.

FIG. 8 illustrates a diagram of an example mapping of sensor input to a force haptic signal that, when played at an actuator, produces a force haptic effect, according to one embodiment of the invention. More specifically, FIG. 8 illustrates sensor 800. Sensor 800 can be identical to sensor 28 of FIG. 1. Sensor 800 can be a sensor configured to detect information. In certain embodiments, sensor 800 can be a sensor configured to detect extra-sensory information, where extra-sensory information is information that cannot normally be perceived by a human being. In other embodiments, sensor 800 can be a sensor configured to detect sensory information, where sensory information is information that can normally be perceived by a human being.

FIG. 8 also illustrates haptic representation module 810. When executed by a processor (not illustrated in FIG. 8), haptic representation module 810 can receive the sensor input from sensor 800, map the sensor input to a force haptic signal, and send the force haptic signal to actuator 820. According to the embodiment, haptic representation module 810 can include an algorithm that maps the sensor input to a force haptic signal, where the force haptic signal is configured to produce a force haptic effect when played at actuator 820. Thus, in certain embodiments, haptic representation module 810 can represent information (which can include sensory information or extra-sensory information) detected by sensor 800 as a force haptic effect that can be played at actuator 820.

In certain embodiments, sensor 800 can be local to haptic representation module 810 (i.e., sensor 800 and haptic representation module 810 can be located within a single device). In other embodiments, sensor 800 is located on a separate device from haptic representation module 810, and the sensor input is sent to haptic representation module 810 over a network.

In certain embodiments, the mapping performed at haptic representation module 810 includes determining whether the received sensor input exceeds a specified threshold (i.e., "specified value"). If the received sensor input exceeds the specified value, a corresponding force haptic signal is generated, and the received sensor input is mapped to the generated force haptic signal. If the received sensor input does not exceed the specified value, no force haptic signal is generated.

In alternate embodiments, the mapping performed at haptic representation module 810 includes mathematically transforming the received sensor input into a corresponding force haptic signal. This can be done continuously as sensor input is received, and thus, the corresponding force haptic signal can be continuously modulated. As the force haptic signal is continuously modulated, the corresponding force haptic effect that is generated can also be continuously modulated.

FIG. 8 also illustrates actuator 820. Actuator 820 can be identical to actuator 26 of FIG. 1. Actuator 820 can receive the force haptic signal sent by haptic representation module 810, and can generate a force haptic effect based on the force haptic signal. In some embodiments, actuator 820 can be a force actuator configured to produce force haptic effects.

Thus, in certain embodiments, actuator 820 can cause a device to apply a static force (such as pressure) to a user of the device. For example, the device can apply a static force to a user as the user grips the device. As another example, the device can apply a static force to the user while the device is in the user's pocket. The static force can be of a sufficient degree that the static force causes the device to deform or change shape. The user can feel the device deform by virtue of the device being in static contact with some part of the user's body. In some embodiments, the device can apply a static force, such that the device deforms only to a degree that the deformation can be felt, but not seen. In other embodiments, the device can apply a static force, such that the device deforms to a sufficient degree so that the user can visually assess the state of the deformation as well. In certain embodiments, actuator 820 can cause a device to apply a dynamic force (such as pressure) to a user of the device, where the device continually applies the force in a rhythmic or periodic way over a period of time.

Figure 9:
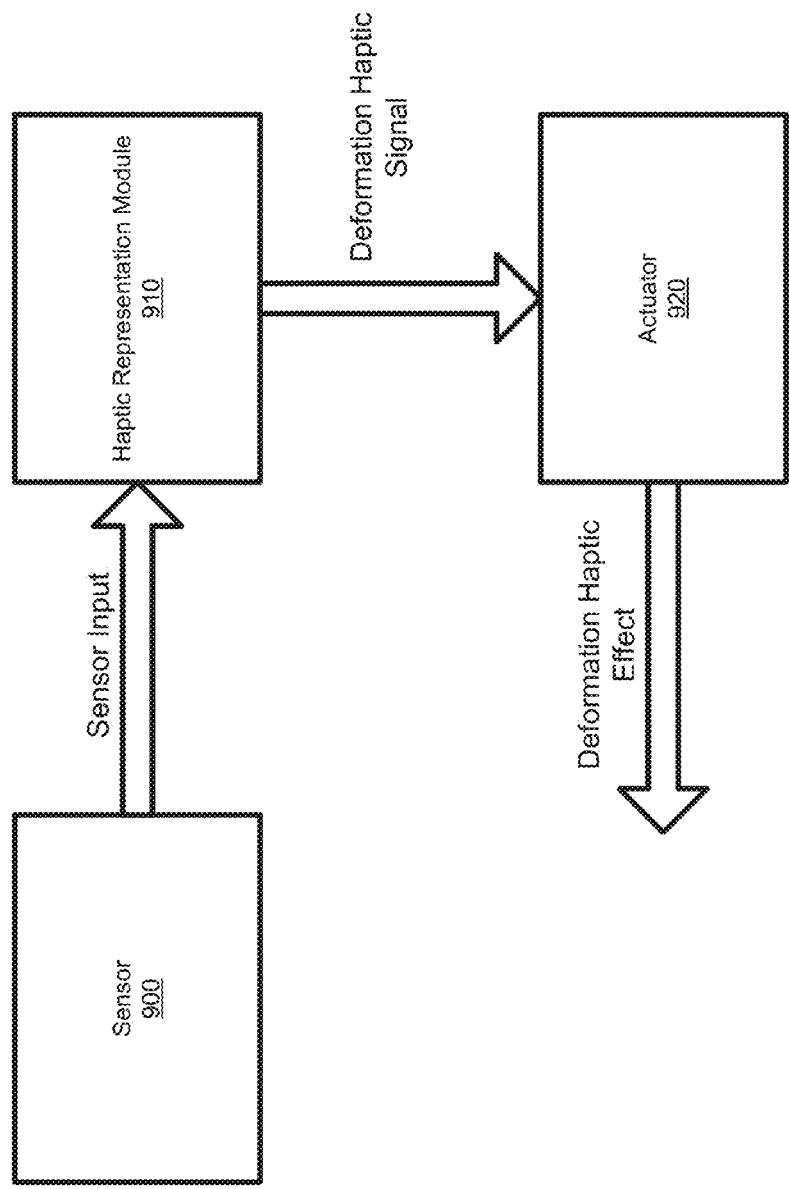
FIG. 9 illustrates a diagram of an example mapping of sensor input to a deformation haptic signal that, when played at an actuator, produces a deformation haptic effect, according to one embodiment of the invention.

FIG. 9 illustrates a diagram of an example mapping of sensor input to a deformation haptic signal that, when played at an actuator, produces a deformation haptic effect, according to one embodiment of the invention. More specifically, FIG. 9 illustrates sensor 900. Sensor 900 can be identical to sensor 28 of FIG. 1. Sensor 900 can be a sensor configured to detect information. In certain embodiments, sensor 900 can be a sensor configured to detect extra-sensory information, where extra-sensory information is information that cannot normally be perceived by a human being. In other embodiments, sensor 900 can be a sensor configured to detect sensory information, where sensory information is information that can normally be perceived by a human being.

FIG. 9 also illustrates haptic representation module 910. When executed by a processor (not illustrated in FIG. 9), haptic representation module 910 can receive the sensor input from sensor 900, map the sensor input to a deformation haptic signal, and send the deformation haptic signal to actuator 920. According to the embodiment, haptic representation module 910 can include an algorithm that maps the sensor input to a deformation haptic signal, where the deformation haptic signal is configured to produce a deformation haptic effect when played at actuator 920. Thus, in certain embodiments, haptic representation module 910 can represent information (which can include sensory information or extra-sensory information) detected by sensor 900 as a deformation haptic effect that can be played at actuator 920.

In certain embodiments, sensor 900 can be local to haptic representation module 910 (i.e., sensor 900 and haptic representation module 910 can be located within a single device). In other embodiments, sensor 900 is located on a separate device from haptic representation module 910, and the sensor input is sent to haptic representation module 910 over a network.

In certain embodiments, the mapping performed at haptic representation module 910 includes determining whether the received sensor input exceeds a specified threshold (i.e., "specified value"). If the received sensor input exceeds the specified value, a corresponding deformation haptic signal is generated, and the received sensor input is mapped to the generated deformation haptic signal. If the received sensor input does not exceed the specified value, no deformation haptic signal is generated.

In alternate embodiments, the mapping performed at haptic representation module 910 includes mathematically transforming the received sensor input into a corresponding deformation haptic signal. This can be done continuously as sensor input is received, and thus, the corresponding deformation haptic signal can be continuously modulated. As the deformation haptic signal is continuously modulated, the corresponding deformation haptic effect that is generated can also be continuously modulated.

FIG. 9 also illustrates actuator 920. Actuator 920 can be identical to actuator 26 of FIG. 1. Actuator 920 can receive the deformation haptic signal sent by haptic representation module 910, and can generate a deformation haptic effect based on the deformation haptic signal. In some embodiments, actuator 920 can be a deformation actuator configured to produce deformation haptic effects.

Thus, in certain embodiments, actuator 920 can cause a device to deform or change shape. In some embodiments, the device can deform only to a degree that the deformation can be felt, but not seen. For example, if the device is in a pocket of a user, the user can reach into his pocket and feel the device and assess the shape of the device. In one example, if the housing of the device is flat, the user has not received any voicemail messages. However, if the housing of the device is extended (i.e., actuator 920 has caused the housing of the device to deform and extend out), then the user has received voicemail messages. In other embodiments, the device can deform to a sufficient degree so that the user can visually assess the state of the deformation as well. In certain embodiments, actuator 920 can cause a device to continually deform in a rhythmic or periodic way over a period of time. For example, the sides of the device can pulse in a way that simulates a breathing pattern. In this example, the device can also display information about its internal state according to how hard or how fast it is "breathing". As another example, the deformation of the device can simulate a heartbeat, and the device can display information about its internal state depending on how hard or fast it is "beating." Furthermore, the device can overlay one or more deformations on top of each other. As an example, the device could deform in a manner to simulate a breathing pattern, and deform in a manner to simulate a heartbeat pattern, simultaneously, but the user would able to differentiate the simultaneous patterns.

Figure 10:
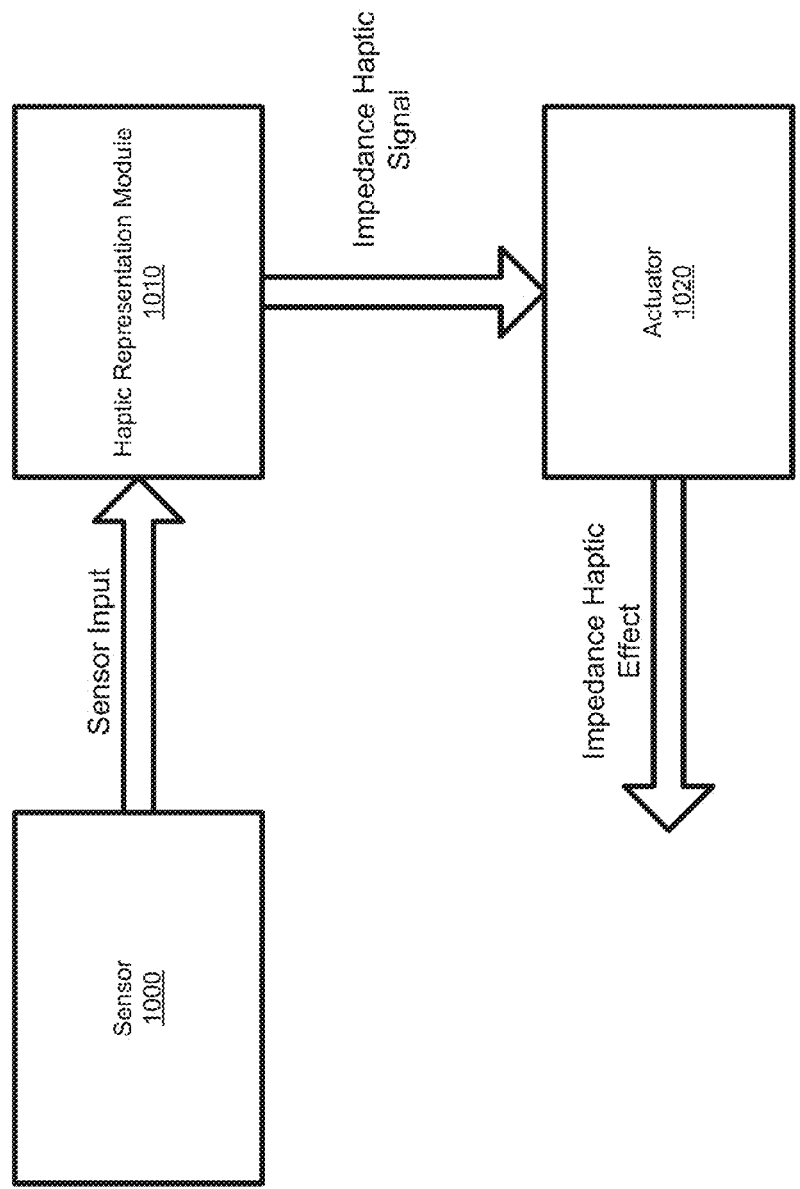
FIG. 10 illustrates a diagram of an example mapping of sensor input to a impedance haptic signal that, when played at an actuator, produces an impedance haptic effect, according to one embodiment of the invention.

FIG. 10 illustrates a diagram of an example mapping of sensor input to a impedance haptic signal that, when played at an actuator, produces an impedance haptic effect, according to one embodiment of the invention. More specifically, FIG. 10 illustrates sensor 1000. Sensor 1000 can be identical to sensor 28 of FIG. 1. Sensor 1000 can be a sensor configured to detect information, such as pressure applied to a device by a user.

FIG. 10 also illustrates haptic representation module 1010. When executed by a processor (not illustrated in FIG. 10), haptic representation module 1010 can receive the sensor input from sensor 1000, map the sensor input to an impedance haptic signal, and send the impedance haptic signal to actuator 1020. According to the embodiment, haptic representation module 1010 can include an algorithm that maps the sensor input to an impedance haptic signal, where the impedance haptic signal is configured to produce an impedance haptic effect when played at actuator 1020. Thus, in certain embodiments, haptic representation module 1010 can represent information (which can include sensory information or extra-sensory information) detected by sensor 1000 as an impedance haptic effect that can be played at actuator 1020.

In certain embodiments, sensor 1000 can be local to haptic representation module 1010 (i.e., sensor 1000 and haptic representation module 1010 can be located within a single device). In other embodiments, sensor 1000 is located on a separate device from haptic representation module 1010, and the sensor input is sent to haptic representation module 1010 over a network.

In certain embodiments, the mapping performed at haptic representation module 1010 includes determining whether the received sensor input exceeds a specified threshold (i.e., "specified value"). If the received sensor input exceeds the specified value, a corresponding impedance haptic signal is generated, and the received sensor input is mapped to the generated impedance haptic signal. If the received sensor input does not exceed the specified value, no impedance haptic signal is generated.

FIG. 10 also illustrates actuator 1020. Actuator 1020 can be identical to actuator 26 of FIG. 1. Actuator 1020 can receive the impedance haptic signal sent by haptic representation module 1010, and can generate an impedance haptic effect based on the impedance haptic signal. In some embodiments, actuator 1020 can be an impedance actuator configured to produce impedance haptic effects.

Thus, in certain embodiments, actuator 1020 can cause a device to produce an impedance haptic effect in response to user input, such as pressure applied to the device by the user. For example, a user may "query" the device to find out a shape of the device, by haptically exploring the contours of the device with a hand or finger. In another example, the user squeezes the device to feel the impedance or deformability. In this way, actuator 1020 can cause the housing of the device to display information to the user, not in a form of deformation, but in a form of mechanical impedance. For example, the user can squeeze the device, and if the device feels "soft," then the user does not have any urgent voicemail messages. However, the user can also squeeze the device, and if the device feels "hard," then the user does have urgent voicemail messages. Thus, the information can be queried by a user in a discreet, intuitive way by applying pressure to the device and ascertaining the amount of mechanical impedance felt.

While the embodiments described above have involved individual force haptic effects, deformation haptic effects, or impedance haptic effects, in alternate embodiments, an actuator can cause a device to produce various combinations of force haptic effects, deformation effects, and impedance haptic effects, as well as vibrotactile effects or any other haptic effects.

Figure 11:
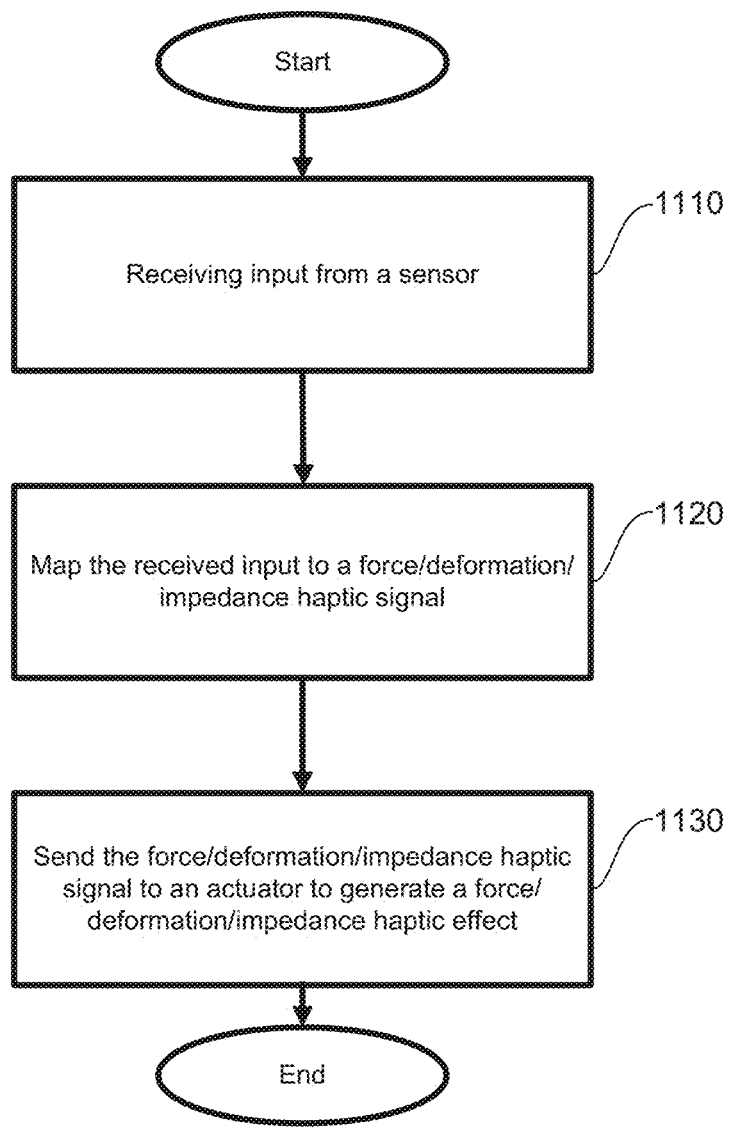
FIG. 11 illustrates a flow diagram of the functionality of a haptic representation module, according to another embodiment of the invention.

FIG. 11 illustrates a flow diagram of the functionality of a haptic representation module (such as haptic representation module 16 of FIG. 1), according to one embodiment of the invention. The flow begins and proceeds to 1110. At 1110, input is received from a sensor. The input can include extra-sensory information, where extra-sensory information is information that cannot normally be perceived by a human being. In certain embodiments, the input can include one or more interaction parameters, where each interaction parameter can include a value.

Also, in certain embodiments, the sensor can be a sensor configured to detect a barometric pressure. In other embodiments, the sensor can be a magnetometer configured to detect an electromagnetic field. In other embodiments, the sensor can be a radiation sensor configured to detect radiation. In other embodiments, the sensor can be a sensor configured to detect a signal sent by a GPS, where the signal can represent a position of a device. In other embodiments, the sensor can be a galvanic skin response sensor configured to detect an electrical conductance of the skin of a user. In other embodiments, the sensor can be a light sensor configured to detect light frequencies, including light frequencies that are within a range of the human eye, and also including light frequencies that are out of range of the human eye. The flow proceeds to 1120.

At 1120, the received input is mapped to a haptic signal. In certain embodiments, the mapping the received input to the haptic signal includes generating the haptic signal when the value of at least one interaction parameter exceeds a specified value. In other embodiments, the mapping the received input to the haptic signal includes continuously modulating the haptic signal based on a continuous updating of the value of at least one interaction parameter. The haptic signal can be a force haptic signal. The haptic signal can be a deformation haptic signal. The haptic signal can be an impedance haptic signal. The haptic signal can be any combination of a force haptic signal, a deformation haptic signal, or an impedance haptic signal. The flow proceeds to 1130.

At 1130, the haptic signal is sent to an actuator to generate a haptic effect. In embodiments where the haptic signal is a force haptic signal, the haptic effect is a force haptic effect. In embodiments where the haptic signal is a deformation haptic signal, the haptic effect is a deformation haptic effect. In embodiments where the haptic signal is an impedance haptic signal, the haptic effect is an impedance haptic effect. In some embodiments where the haptic effect is a force haptic effect, the force haptic effect can cause a device to apply a static force to a user. In other embodiments where the haptic effect is a force haptic effect, the force haptic effect can cause the device to apply a dynamic force to the user. In certain embodiments where the haptic effect is a force haptic effect, the force haptic effect can cause the device to apply pressure to the user's body. In certain embodiments where the haptic effect is a deformation haptic effect, the deformation haptic effect can cause a device to deform. In other embodiments where the haptic effect is a deformation haptic effect, the deformation haptic effect can cause the device to continuously deform over a period of time. In certain embodiments where the haptic effect is a deformation haptic effect, the deformation haptic effect can cause the device to modify at least one of a macro-shape of the device or a texture of the device, and the deformation of the devices can comprise at least one of a visual deformation, a haptic deformation, a quasi-static deformation, or a dynamic deformation. In embodiments where the haptic effect is an impedance haptic effect, the impedance haptic effect can cause a device to produce a mechanical impedance in response to user input. In certain embodiments where the haptic effect is an impedance haptic effect, the impedance haptic effect can cause the device to stiffen in response to pressure that is applied to the device by a user.

In embodiments where the sensor is a sensor configured to detect a barometric pressure, the haptic effect that is generated by the actuator can cause a device to deform based on the detected barometric pressure. In embodiments where the sensor is a magnetometer configured to detect an electromagnetic field, the haptic effect that is generated by the actuator can cause a device to deform based on one or more properties of the detected electromagnetic field. In embodiments where the sensor is a radiation sensor configured to detect radiation, the haptic effect that is generated by the actuator can cause a device to deform based on the detected radiation. In embodiments where the sensor is a sensor configured to detect a signal sent by a GPS, where the signal represents a position of a device, the haptic effect that is generated by the actuator can cause the device to deform based on the detected signal. In embodiments where the sensor is a galvanic skin response sensor configured to detect an electrical conductance of the skin of a user, the haptic effect that is generated by the actuator can cause the device to deform based on one or more characteristics of the user identified from the detected electrical conductance of the skin of the user. In embodiments where the sensor is a light sensor configured to detect light frequencies, including light frequencies that are within a range of the human eye, and also including light frequencies that are out of range of the human eye, the haptic effect that is generated by the actuator can cause a display of the device to deform based on the detected light frequencies that are out of range of the human eye. The flow then ends.

Thus, a haptic representation system is provided that represents sensor input as one or more haptic effects. The haptic representation system can enable richer, more informative, and more interactive experiences for a user. The haptic representation system has wide ranging use cases, such as military, medical, automotive, and mobility.

The features, structures, or characteristics of the invention described throughout this specification may be combined in any suitable manner in one or more embodiments. For example, the usage of "one embodiment," "some embodiments," "certain embodiment," "certain embodiments," or other similar language, throughout this specification refers to the fact that a particular feature, structure, or characteristic described in connection with the embodiment may be included in at least one embodiment of the present invention. Thus, appearances of the phrases "one embodiment," "some embodiments," "a certain embodiment," "certain embodiments," or other similar language, throughout this specification do not necessarily all refer to the same group of embodiments, and the described features, structures, or characteristics may be combined in any suitable manner in one or more embodiments.

One having ordinary skill in the art will readily understand that the invention as discussed above may be practiced with steps in a different order, and/or with elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

We claim:

1. A method of generating a haptic effect comprising:
   receiving input from a sensor, wherein the input comprises extra-sensory information;
   mapping the received input to a deformation haptic signal comprising modulating the deformation haptic signal based on an updating of the input; and
   sending the deformation haptic signal to an actuator coupled to a device to generate the haptic effect, wherein the haptic effect comprises a deformation of the device.

2. The method of claim 1, wherein the received input comprises interaction parameters, wherein each interaction parameter comprises a value;
   the mapping the received input to the deformation haptic signal further comprising generating the deformation haptic signal when the value of an interaction parameter exceeds a specified value.

3. The method of claim 1, wherein the sensor is in contact with a user's skin, and the input is an electrical conductance of the skin.

4. The method of claim 1, wherein the device comprises a housing and the deformation comprises altering a shape of the housing.

5. The method of claim 4, wherein the haptic effect provides directional information.

6. The method of claim 4, wherein the haptic effect emulates a handshake or heartbeat.

7. A non-transitory computer readable medium having instructions stored thereon that, when executed by a processor, cause the processor to generate a haptic effect, the generating the haptic effect comprising:
   receiving input from a sensor, wherein the input comprises extra-sensory information;
   mapping the received input to a deformation haptic signal comprising modulating the deformation haptic signal based on an updating of the input; and
   sending the deformation haptic signal to an actuator coupled to a device to generate the haptic effect, wherein the haptic effect comprises a deformation of the device.

8. The computer readable medium of claim 7, wherein the received input comprises interaction parameters, wherein each interaction parameter comprises a value;
   the mapping the received input to the deformation haptic signal further comprising generating the deformation haptic signal when the value of an interaction parameter exceeds a specified value.

9. The computer readable medium of claim 7, wherein the sensor is in contact with a user's skin, and the input is an electrical conductance of the skin.

10. The computer readable medium of claim 7, wherein the device comprises a housing and the deformation comprises altering a shape of the housing.

11. computer readable medium of claim 10, wherein the haptic effect provides directional information.

12. The computer readable medium of claim 10, wherein the haptic effect emulates a handshake or heartbeat.

13. A haptic representation system comprising:
    a memory configured to store a haptic representation module;
    a processor configured to execute the haptic representation module stored on the memory; and
    an actuator configured to output a haptic effect;
    wherein the haptic representation module is configured to receive input from a sensor, wherein the input comprises extra-sensory information;
    wherein the haptic representation module is further configured to map the received input to a deformation haptic signal comprising modulating the deformation haptic signal based on an updating of the input;
    wherein the haptic representation module is further configured to send the deformation haptic signal to the actuator to generate the haptic effect, wherein the haptic effect comprises a deformation of the system.

14. The haptic representation system of claim 13, wherein the received input comprises interaction parameters, wherein each interaction parameter comprises a value;
    the mapping the received input to the deformation haptic signal further comprising generating the deformation haptic signal when the value of an interaction parameter exceeds a specified value.

15. The haptic representation system of claim 13, wherein the sensor is in contact with a user's skin, and the input is an electrical conductance of the skin.

16. The haptic representation system of claim 13, further comprising a housing, wherein the deformation comprises altering a shape of the housing to provide directional information.

17. The haptic representation system of claim 13, wherein the haptic effect emulates a handshake or heartbeat.

18. The method of claim 3, wherein the deformation of the device is based on one or more characteristics of the user identified from the electrical conductance.

19. The computer readable medium of claim 9, wherein the deformation of the device is based on one or more characteristics of the user identified from the electrical conductance.

20. The haptic representation system of claim 15, wherein the deformation of the system is based on one or more characteristics of the user identified from the electrical conductance.

* * * * *